US012187658B1

(12) United States Patent
Haynes et al.

(10) Patent No.: US 12,187,658 B1
(45) Date of Patent: Jan. 7, 2025

(54) **APPLICATION OF MESOPOROUS SILICA NANOPARTICLES TO MEMBERS OF THE FAMILY OF *CUCURBITACEAE***

(71) Applicants: Regents of the University of Minnesota, Minneapolis, MN (US); The Connecticut Agricultural Experiment Station, New Haven, CT (US)

(72) Inventors: Christy Haynes, Minneapolis, MN (US); Joseph Buchman, St. Paul, MN (US); Wade Elmer, Wallingford, CT (US); Jason White, Prospect, CT (US); Chuanxin Ma, Amherst, MA (US)

(73) Assignees: Regents of the University of Minnesota, Minneapolis, MN (US); The Connecticut Agricultural Experiment Station, New Haven, CT (US)

( * ) Notice: Subject to any disclaimer, the term of this patent is extended or adjusted under 35 U.S.C. 154(b) by 954 days.

(21) Appl. No.: 17/024,489

(22) Filed: Sep. 17, 2020

Related U.S. Application Data

(60) Provisional application No. 62/902,865, filed on Sep. 19, 2019.

(51) Int. Cl.

| | |
|---|---|
| ***C01B 33/18*** | (2006.01) |
| ***A01C 1/06*** | (2006.01) |
| ***C05D 9/00*** | (2006.01) |
| *B82Y 5/00* | (2011.01) |

(52) U.S. Cl.

CPC ................ *C05D 9/00* (2013.01); *C01B 33/18* (2013.01); *B82Y 5/00* (2013.01); *C01P 2004/32* (2013.01);

(Continued)

(58) Field of Classification Search

None

See application file for complete search history.

(56) References Cited

U.S. PATENT DOCUMENTS

| | | | | |
|---|---|---|---|---|
| 11,130,679 | B2 * | 9/2021 | Moghaddam | C01B 33/18 |
| 2019/0174765 | A1 * | 6/2019 | Carney | C12N 1/12 |
| 2022/0009848 | A1 * | 1/2022 | Traxler | C10B 53/02 |

FOREIGN PATENT DOCUMENTS

| | | | | | |
|---|---|---|---|---|---|
| RU | 2654814 | C1 * | 5/2018 | | A01C 1/06 |
| WO | WO 2016/027112 | A1 * | 2/2016 | | A01N 3/00 |
| WO | WO 2019/159201 | A1 * | 8/2019 | | C05G 3/02 |

OTHER PUBLICATIONS

Pulkit Bindra et al, "Nano-hives for plant stimuli controlled targeted iron fertilizer application", Chemical Engineering Journal 375 (2019) 121995.*

(Continued)

*Primary Examiner* — Wayne A Langel

(74) *Attorney, Agent, or Firm* — Westman, Champlin & Koehler, P.A.; Z. Peter Sawicki; Amanda M. Prose

(57) ABSTRACT

A method improves yield and/or combats *Fusarium* wilt in a member of the family Cucurbitaceae wherein the method comprises applying mesoporous silica nanoparticles to a seed or plant of the member of the family Cucurbitaceae. Chitosan may be used in combination with the mesoporous silica nanoparticles. The mesoporous silica nanoparticles are usable as an agricultural amendment with or without the chitosan. Of particular interest is watermelon (*Citrullus lanatus*). When seeds of *Citrullus lanatus* are infused with mesoporous silica nanoparticles with or without the chitosan increased germination was observed.

16 Claims, 8 Drawing Sheets

(52) U.S. Cl.
CPC ...... *C01P 2004/64* (2013.01); *C01P 2006/16* (2013.01)

(56) References Cited

OTHER PUBLICATIONS

Pengyue Zhao et al, "Translocation, distribution and degradation of prochloraz-loaded mesoporous silica nanoparticles in cucumber plants", Nanoscale, 2018, 10, 1798-1806.*

Pengyue Zhao et al, enhancement of Spirotetramat Transfer in Cucumber Plant Using Mesoporous Silica Nanoparticles as Carriers J. Agric. Food Chem. 2018, 66, 11592-11600.*

Yang, L. et al. "Synergistic effect of oligochitosan and silicon on inhibition of Monilinia fructicola infections." J. Sci. Food Agric., 2010, 90, 630-634.

Nguyen, N.T. et al. "New oligochitosan-nanosilica hybrid materials: preparation and application on chili plants for resistance to anthracnose disease and growth enhancement" Polymer Journal, 2017, 49, 861-869.

Xu, C. et al. "Emulsion-based synchronous pesticide encapsulation and surface modification of mesoporous silica nanoparticles with carboxymethyl chitosan for controlled azoxystrobin release" Chemical Engineering Journal, 2018, 348, 244-254.

Bhaskara Reddy, M. V., et al. "Chitosan Treatment of Wheat Seeds Induces Resistance to Fusarium Graminearum and Improves Seed Quality" J. Agric. Food Chem. 1999, 47, 1208-1216.

* cited by examiner

APPLICATION OF MESOPOROUS SILICA NANOPARTICLES TO MEMBERS OF THE FAMILY OF *CUCURBITACEAE*

CROSS REFERENCE TO RELATED APPLICATION

This application claims priority to and the benefit of U.S. provisional patent application Ser. No. 62/902,865, filed on Sep. 19, 2019, the content of which is hereby incorporated in its entirety.

This invention was made with government support under CHE-1503408 awarded by the National Science Foundation. The government has certain rights in the invention.

BACKGROUND

This disclosure relates to the application of mesoporous silica nanoparticles with or without a chitosan coating to a seed or plant of the family Cucurbitaceae. In particular this disclosure relates to the application of mesoporous silica nanoparticles with or without a chitosan coating to a seed or plant of watermelon (*Citrullus lanatus*).

Each year, approximately 20-40% of agricultural crops are lost to disease, contributing significantly to global food insecurity. Soil-borne fungal pathogens, such as *Fusarium oxysporum* f. sp. *niveum* (FON), infect the root systems of watermelon (*Citrullus lanatus*). After infecting the root system, the pathogen colonizes the vascular tissue, disrupting water transport within the plant, causing the symptomatic wilt, compromised growth, and potentially plant death. For watermelon, *Fusarium* wilt is one of the major factors limiting global fruit production. This resistant fungus is capable of surviving up to six years in soil without the presence of a host, making it a particularly challenging pathogen to manage. According to the 2017 USDA Economic Research Service, over 45,000 ha of watermelons were grown in the US, producing over 40 million pounds. The discontinued use of effective fumigant treatments and the increased growth of highly susceptible seedless watermelon varieties have been associated with enhanced *Fusarium* wilt damage.

Although not essential, beneficial elements such as silicon play important roles in initiating the defense response of certain plants against diseases, insects, and stress. While silicon accumulation is more commonly observed in monocotyledons, the family Cucurbitaceae are one of a few groups of dicotyledons known to accumulate significant amounts of silicon. Silicon is acquired through roots as silicic acid and will often polymerize, forming silica phytoliths that fortify the plant's cell wall. This enhanced barrier makes it more challenging for pathogens to penetrate and infect the plant tissues. Silicon is capable of stimulating plant metabolic defense mechanisms against disease by stimulating the activity of defense-related enzymes, such as polyphenoloxidase or chitinase, as well as inducing production of defense-related compounds like flavonoids and phytoalexins. While most studies have focused on root-absorbed silicon, a few reports have demonstrated that foliarly applied silica salts will reduce disease. However, one limitation with silica applications is that the silicon supply to the plant must be continuous or the disease-suppressing effects will be reduced or non-existent. One method with great potential for the efficient delivery of beneficial elements such as silicon is the use of slow-dissolving or controlled release nanoparticles for nutrient delivery. Although many elements such as silicon and copper are not translocated basipetally, nanoscale forms of these nutrients have been shown to translocate from shoots to roots. For copper, this more effective translocation has been associated with greater disease suppression in *Fusarium*-infected watermelon and tomato. A formulation of silica called mesoporous silica was first reported in 1992, and these materials are characterized by high surface areas and pore volumes, making them useful for many applications, potentially including slow release of silicic acid as the large surface area contacts the aqueous environment. The uptake and distribution of mesoporous silica nanoparticles in wheat, lupin, and *Arabidopsis* have been demonstrated.

Other organic compounds such as chitosan have also been shown to be important in plant disease resistance. While there is some evidence of direct antifungal behavior from chitosan, its greater effect is to initiate a signaling cascade within plants to bolster their natural defense mechanisms. In fact, chitosan has been applied as a treatment for suppressing plant disease. For example, Bhaskara Reddy et al. demonstrated that *Fusarium graminearum* infection was controlled by treating wheat seeds with chitosan, which led to a >85% germination of seeds, and reduced the transmission of the fungus to the seedlings' primary roots. (Bhaskara Reddy, M. V; Arul, J.; Angers, P.; Couture, L. Chitosan Treatment of Wheat Seeds Induces Resistance to *Fusarium Graminearum* and Improves Seed Quality. J. Agric. Food Chem. 1999, 47, 1208-1216.) Other benefits of a chitosan treatment include increased plant growth and overall fruit production, as evident in the ~50% increase in fruit production from both chili and strawberry plants after chitosan application. Due to their different pathways to promote disease resistance, chitosan can be combined and co-treated with silica, and together, they have been shown to further enhance disease suppression. (Nguyen, N. T.; Nguyen, D. H.; Pham, D. D.; Dang, V. P.; Nguyen, Q. H.; Hoang, D. Q. New Oligochitosan-Nanosilica Hybrid Materials: Preparation and Application on Chili Plants for Resistance to Anthracnose Disease and Growth Enhancement. Polym. J. 2017, 49 (12), 861-869) (Yang, L.; Zhao, P.; Wang, L.; Filippus, I.; Meng, X. Synergistic Effect of Oligochitosan and Silicon on Inhibition of Monilinia Fructicola Infections. J. Sci. Food Agric. 2010, 90 (4), 630-634.)

SUMMARY

This disclosure describes a method for improving yield in a member of the family Cucurbitaceae wherein the method comprises applying mesoporous silica nanoparticles to a seed or plant of the member of the family Cucurbitaceae.

In another embodiment the method further comprises applying to the seed or plant chitosan in combination with the mesoporous silica nanoparticles.

In another embodiment the member of the family Cucurbitaceae comprises *Citrullus lanatus.*

In another embodiment the plant of the *Citrullus lanatus* demonstrated reduced expression of stress-related genes.

In another embodiment the plant of the *Citrullus lanatus* exhibited an increase of approximately at least 70% in fruit by weight.

In another embodiment the method further comprises the mesoporous silica nanoparticles being applied to the plant of the member of the family Cucurbitaceae by foliar exposure with the mesoporous silica nanoparticle suspension.

In another embodiment the method further comprises the mesoporous silica nanoparticles being applied to the seed of the member of the family Cucurbitaceae by infusing the seed with the mesoporous silica nanoparticle suspension.

In a further embodiment an agricultural amendment comprises mesoporous silica nanoparticles in a form adaptable for application to a seed or a plant.

In a further embodiment the agricultural amendment further comprises chitosan in combination with the mesoporous silica nanoparticles.

In yet another embodiment a method of this disclosure infuses seeds from a member of the family Cucurbitaceae with mesoporous silica nanoparticles by providing a suspension of the mesoporous silica nanoparticles and placing the seeds in the mesoporous silica nanoparticle suspension. The seeds in the mesoporous silica nanoparticle suspension are then placed in a vacuum chamber where a vacuum is pulled. The vacuum is then released thereby infusing the seeds with the mesoporous silica nanoparticle suspension.

In another embodiment the method further comprises planting the seeds in a growing medium wherein increased germination of the seeds results when compared to seeds that have not been infused with the mesoporous silica nanoparticle suspension.

In another embodiment the member of the family Cucurbitaceae comprises *Citrullus lanatus.*

In another embodiment the mesoporous silica nanoparticle suspension comprises chitosan in combination with the mesoporous silica nanoparticles.

In another further embodiment of this disclosure a method for combating *Fusarium* wilt in a member of the family Cucurbitaceae is described wherein the method comprises applying mesoporous silica nanoparticles to a seed or plant of the member of the family Cucurbitaceae.

In another embodiment the method further comprises applying to the seed or plant chitosan with the mesoporous silica nanoparticles.

In another embodiment, the member of the family Cucurbitaceae comprises *Citrullus lanatus.*

In another embodiment, the plant of the *Citrullus lanatus* demonstrated reduced expression of stress-related genes.

In another embodiment, the plant of the *Citrullus lanatus* exhibited an increase of approximately at least 70% in fruit by weight.

In another embodiment, the mesoporous silica nanoparticles were applied to the plant of the member of the family Cucurbitaceae by foliar exposure with the mesoporous silica nanoparticle suspension.

In another embodiment, the mesoporous silica nanoparticles were applied to the seed of the member of the family Cucurbitaceae by infusing the seed with the mesoporous silica nanoparticle suspension.

DETAILED DESCRIPTION

Figure 1A:
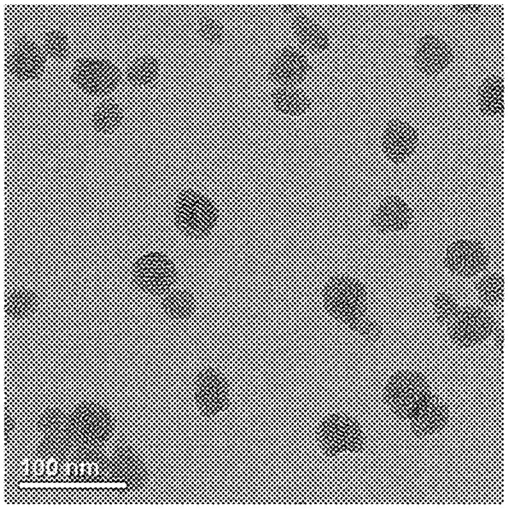
FIG. 1A is a Representative TEM image of bare mesoporous silica nanoparticles (MSNs).

This disclosure describes a method for improving yield in a member of the family Cucurbitaceae, particularly watermelon (*Citrullus lanatus*) by applying mesoporous silica nanoparticles to a seed or plant of watermelon. When chitosan was coated on the mesoporous silica nanoparticles yield in watermelon was improved by approximately 70%.

These chitosan-coated mesoporous silica nanoparticles were then applied to plants by various methods (i.e. dipping seedlings in a nanoparticle suspension to coat the leaves or other methods for exposing the leaves to the nanoparticle suspension, or using a vacuum infiltration method to load the seeds) to improve crop production as well as to combat fungal disease. In some instances, a vacuum infiltration method was used to load the seeds with these nanoparticles, where the seeds were placed in a nanoparticle suspension, and then moved to a vacuum chamber where a vacuum was pulled and slowly released so that the seed pockets were backfilled with the nanoparticle suspension.

Where high surface area mesoporous silica nanoparticles and chitosan are combined and applied to plants, plant health was improved without the need for an additional pesticide. Plant health was assessed by monitoring the total biomass and fruit production in both healthy and pathogen-infected plants up to 100 days after a single nanoparticle application (500 mg/L) was applied at the seedling stage. Both types of mesoporous silica nanoparticles (with or without chitosan) enhanced the innate defense mechanisms of watermelon, with mesoporous silica nanoparticles (MSNs) and chitosan-coated mesoporous silica nanoparticles (CTS-MSNs) reducing disease severity by ~40% and ~27%, respectively, as measured by the area-under-the-disease-progress curve. Changes in gene expression measured several weeks after nanoparticle application demonstrated reduced expression of several stress-related genes after CTS-MSN and MSN treatments, indicating a reduced disease burden on the plant. Although treatment did not impact fruit production from diseased plants, a single application of chitosan-coated mesoporous silica nanoparticles at the seedling stage led to a 70% increase in the fruit yield of uninfected watermelon. Monitoring plant biomass revealed that MSNs and CTS-MSNs had no significant impact on the biomass reductions in diseased plants, likely because seedlings were treated and biomass was measured weeks later in the fully grown plants. These findings demonstrate the utility of a single application of mesoporous silica nanoparticles with or without a chitosan coating as a nano-enabled agricultural amendment.

Both mesoporous silica nanoparticles and chitosan-coated mesoporous silica nanoparticles were applied to *C. lanatus* to determine their ability to aid in defense against *Fusarium* wilt. Both silicon and chitosan are environmentally safe materials; silicon is the second most abundant element in Earth's crust, and chitosan is derived from chitin, the second most abundant renewable carbon source, making use of these materials in agriculture is quite sustainable. Mesoporous silica nanoparticles (MSNs) were employed because of their high surface area, which could facilitate faster degradation to monosilicic acid than nonporous silica. In one example, the average surface area was approximately 700 $cm^2/g$. The ability to load various cargo (i.e. nutrients) within the nanostructure for a synergistic delivery platform is also part of this disclosure. By mesoporous nanoparticles is meant that the particles contain pores with diameters between 2 and 50 nm, according to IUPAC nomenclature. For comparison, IUPAC defines microporous material as a material having pores smaller than 2 nm in diameter and macroporous material as a material having pores larger than 50 nm in diameter. In one example, the nanoparticles used in this disclosure were about 4 nm.

A novel vacuum-infiltration technique was used to pretreat watermelon seeds with MSNs and CTS-MSNs, investigating their effect on germination. The seeds were placed in a nanoparticle suspension, and then moved to a vacuum chamber where a vacuum was pulled and slowly released so that the seed pockets were backfilled with nanoparticle suspension.

Plants were also treated with MSNs or CTS-MSNs to assess the growth, biomass, and fruit yield in the presence of pathogenic *Fusarium* wilt. The silicon content in plant tissues was determined by inductively coupled plasma-mass spectrometry (ICP-MS), and quantitative reverse transcription polymerase chain reaction (RT-qPCR) was used to assess the expression of genes related to host defense. The findings show that a single application of these materials could significantly reduce disease progress in infected plants and in healthy plants, treatment with CTS-MSN significantly increased fruit production.

EXAMPLES

Materials

Tetraethylorthosilicate (TEOS), cetyltrimethylammonium bromide (CTAB), and chitosan (50-190 kDa) were obtained from Sigma-Aldrich (St. Louis, MO). Ammonium hydroxide ($NH_4OH$, 28-30% as $NH_3$) was purchased from Avantor Performance Materials (Center Valley, PA). Chlorotrimethyl silane was purchased from Fluka. Ammonium nitrate ($NH_4NO_3$) was acquired from Mallinckrodt (St. Louis, MO) and 2-[methoxy(polyethyleneoxy)$_{9-12}$propyl]-trimethoxysilane, tech 90 (PEG-silane, molecular weight 591-723 g/mol, 9-12 EO) was obtained from Gelest, Inc. (Morrisville, PA). Absolute ethanol was acquired from Pharmco-Aaper (Brookfield, CT). Ultrapure water (18.2 MΩ·cm resistivity) was purified from a Milli-Q Millipore water purification system (Billerica, MA). Watermelon seeds (*Citrullus lanatus* Thunb. cv Sugar Baby) were acquired from Harris Seed Co. (Rochester, NY) and the ProMix BX potting mix was purchased from Premier Hort Tech (Quakertown, PA). Peter's soluble 20-10-20 N-P-K fertilizer was obtained from R. J. Peter's Inc. (Allentown, PA).

Synthesis of Mesoporous Silica Nanoparticles (MSNs)

MSNs were synthesized by adapting an established protocol. (Lin, Y.-S.; Abadeer, N.; Hurley, K. R.; Haynes, C. L. Ultrastable, Redispersible, Small, and Highly Organomodified Mesoporous Silica Nanotherapeutics. J. Am. Chem. Soc. 2011, 133 (50), 20444-20457.) Briefly, cetyltrimethylammonium bromide (0.29 g) was mixed with 0.256 M $NH_4OH$ (150 mL) with stirring (1 hr, 300 rpm, 50° C.) to form a surfactant template. Tetraethylorthosilicate (2.5 mL, 0.88 M) in ethanol was then added dropwise and stirred (1 hr, 600 rpm, 50° C.), forming the silica structure around the CTAB micelles. Then, 2-[methoxy(polyethyleneoxy)$_{9-12}$propyl]-trimethoxysilane (450 μL) was added slowly and stirred (30 min, 600 rpm, 50° C.), followed by addition of chlorotrimethylsilane (68 μL) to modify the silica surface for dispersion stability. The beaker was immediately covered, and then the mixture was stirred (30 min, 600 rpm, 50° C.). Afterward, the cover was removed, and the MSNs were aged at 50° C. for ~20 hours.

The MSNs were purified with ultracentrifugation (30 min, 61,579×g) followed by resuspension in 6 g/L $NH_4NO_3$ (50 mL), which was refluxed for 1 hr (300 rpm, 60° C.). After reflux, the suspension was ultracentrifuged for 20 min at 61,579×g (all subsequent ultracentrifugation steps used this duration and speed), resuspending the pellet in 95% ethanol. This suspension was again ultracentrifuged, resuspended in 6 g/L $NH_4NO_3$ (50 mL) and refluxed (1 hr, 300 rpm, 60° C.). The suspension was then ultracentrifuged three more times, and resuspended in increasing ethanol concentrations (95%, 99%, 99% ethanol in water), and the final suspension was dried using a rotary evaporator to collect the powdered MSN product.

Coating MSNs with Chitosan

To coat the MSNs with chitosan, a procedure from Chen et al was adapted (Chen, F.; Zhu, Y. Chitosan Enclosed Mesoporous Silica Nanoparticles as Drug Nano-Carriers: Sensitive Response to the Narrow PH Range. Microporous Mesoporous Mater. 2012, 150 (1), 83-89.) The chitosan coating adheres to the silica due to hydrogen bonding between the surface silanol groups of MSNs and amine groups on chitosan. A 0.6% w/v solution of chitosan was prepared in 10% v/v aqueous acetic acid. The pH was then adjusted to 6.0 using 1 M NaOH. Dried MSNs were added to the chitosan solution with magnetic stirring to prepare a 0.5% w/v suspension, typically with 100 mg of MSNs added to 20 mL chitosan solution. The suspension was then stirred at room temperature for 48 hours. Excess chitosan was removed via ultracentrifugation at 6842×g for 15 minutes. CTS-MSNs were then re-dispersed in water and collected by rotary evaporation. To characterize the chitosan coating, TEM imaging was used (described below), as well as determination of the hydrodynamic diameter and zeta potential. Changes in the porosity and surface area of the material were monitored with nitrogen physisorption, and the amount of chitosan coating was quantified using thermogravimetric analysis (TGA).

Transmission Electron Microscopy

To prepare the MSNs for imaging with TEM, the particles were diluted to 0.5 mg/mL in ethanol and sonicated for 10 min to ensure dispersity. Afterward, 200 mesh copper grids with Formvar and carbon supports (Ted Pella, Inc., Redding, CA) were dipped in the suspension and allowed to air dry for 10 min. For the CTS-MSNs, they were first diluted to 0.5 mg/mL in water and sonicated for 10 min. Then, 3 μL of the suspensions were drop-cast onto TEM grids which were allowed to air dry overnight. Images were acquired using an FEI Tecnai T12 transmission electron microscope that was used at 120 kV operating voltage. To determine the size of the MSNs, the images were analyzed using ImageJ[36] to measure the diameter of at least 500 randomly selected nanoparticles.

Hydrodynamic Diameter and Zeta Potential Measurements

After synthesis of the MSNs and coating of CTS-MSNs, the nanoparticles were suspended in water at 500 mg/L. The nanoparticles were sonicated for 10 min to ensure that they were well-dispersed. The hydrodynamic diameters and ζ-potentials were then determined using a Brookhaven Zeta-PALS instrument (Holtsville, NY).

Nitrogen Physisorption

Nitrogen physisorption was used to determine the surface area and pore volume of the MSNs and CTS-MSNs, and was utilized to confirm loading of chitosan onto the MSN surface. Approximately 15 mg of MSN were added (for CTS-MSNs, >60 mg were required) to the sample holder. The samples were degassed prior to analysis with a Micromeritics ASAP™ 2020 (Norcross, GA). The surface area and pore volume were determined using the BET method.

Thermogravimetric Analysis

Thermogravimetric analysis was used to assess the amount of chitosan on the MSN surface. MSNs and CTS-MSNs were first thoroughly dried using a rotary evaporator overnight. Then, ~10 mg of material were weighed onto an aluminum pan and placed onto a platinum tray. This was analyzed using a TA Instruments Q500 TGA (New Castle, DE) operated in a temperature range from 25-550° C. (ramp rate: 10° C./min) using 100 mL/min nitrogen gas (40 mL/min for balance, 60 mL/min for sample).

Preparation of Millet Inoculum

*F. oxysporum* f. sp. *niveum* (FON) was isolated from infected watermelon seeds in 2011 and since then, monosporic cultures were stored at 4° C. The FON inoculum was increased on sterile Japanese millet and ground in a mill using a previously published protocol. (Elmer, W.; De La Torre-Roche, R.; Pagano, L.; Majumdar, S.; Zuverza-Mena, N.; Dimkpa, C.; Gardea-Torresdey, J.; White, J. C. Effect of Metalloid and Metal Oxide Nanoparticles on *Fusarium* Wilt of Watermelon. Plant Dis. 2018, 102 (7), 1394-1401.) This FON millet inoculum was used to infest potting soil at 0.75 g/liter potting soil prior to transplanting MSN-treated watermelon plants.

Nanoparticle Application to *Citrullus lanatus*

To investigate the effect of nanoparticle application on the germination of watermelon seeds, the seeds were dosed with nanoparticles using a novel vacuum-infiltration technique that takes advantage of the air pockets in seed coats. One hundred watermelon seeds (*Citrullus lanatus* Thunb. cv Sugar Baby, Harris Seed Co., Rochester, NY) were placed in 30 mL suspensions of MSNs, CTS-MSNs, chitosan (250 and 500 mg/L each), or water. The solutions were moved to a desiccating chamber and were placed under vacuum using a vacuum pump for 10 min. The pressure was reduced to 0.6 Torr for 10 min, and then the vacuum was slowly released, which allows the seed coat air pockets to be backfilled with the nanoparticle-containing suspensions. Seeds were removed, drained, and immediately placed into 10 cm pots filled with FON-infested or non-infested potting soil (Pro-Mix BX, Premier Hort Tech, Quakertown, PA). Approximately 20 seeds from each treatment were dried at 80° C. for 48 hr, ground, and digested for ICP analysis described below to assess the silicon content. There were 10 replicate pots with five seeds per pot. Seedling emergence and growth was monitored for 14 days. To monitor the impact on plant growth and disease resistance, watermelon seeds were first germinated in ProMix BX potting mix. Three weeks later, they were fertilized with Peter's soluble 20-10-20 N-P-K fertilizer (40 mL, R. J. Peter's Inc., Allentown, PA). One week after application of fertilizer, the watermelon plants were inverted and dipped for approximately 5 sec in 500 mg/L suspensions of MSNs, CTS-MSNs, chitosan, or bulk silica that had been amended with Regulaid nonionic surfactant (1 mL/L) (to enhance particle adhesion on the leaf surface), taking care to keep the roots unexposed. In the dipping process, each plant received approximately 1.5 mL of suspension. These suspensions had been probe sonicated for 2 min prior to this application to ensure particle dispersion. Plants were allowed to drain and dry upside down to minimize root contact with the nanoparticle amendments. Plants were then used in greenhouse and field trials.

For initial greenhouse growth, the plants were transplanted into pots containing either pathogen-free ProMix BX potting mix or potting mix with 0.75 g of millet inoculum per L of potting mix. These pots were kept in a greenhouse for the duration of the study. Select plants were transplanted to two locations (Griswold, CT and Hamden, CT) to monitor disease progress, plant growth, and fruit production under field conditions. Millet inoculum (~2 g) had been hand mixed into the planting holes (approximately 2 L volume of soil) for the *Fusarium*-infested treatment groups. There were twelve replicate plots (one plant per plot) in each treatment, with six plots being exposed to the FON pathogen and six plots being pathogen-free.

Monitoring Seed Germination after Vacuum Infiltration of NPs

To assess seed germination, the seeds that were vacuum-infiltrated with NPs as described above and were planted into pots containing pathogen-free potting mix or 0.75 g millet inoculum/L potting mix. Seeds began to emerge on day 4 and were counted daily for 2 weeks. The cumulative seed germination was plotted and the area-under-the-seed-germination curve (AUSGC) was calculated using the trapezoid rule (Equation 1):

$$AUSGC=\Sigma[S_i+S_{(i+1)}]/2\times(t_{(i+1)}-t_i) \quad (1)$$

$S_i$ is the number of seeds that had germinated at time, $t_i$. These values were computed in the same manner as the area-under-the-disease-progress curve, described below.

Monitoring Disease Progress

At 31, 61, and 95 days post-planting, the watermelon plants at were assessed for the severity of *Fusarium* wilt, using a i to 5 scale (1=no disease symptoms, 2=slightly stunted, 3=stunted and/or partially wilted, 4=completely wilted, and 5=dead). The cumulative severity ratings on the plants were plotted as a function of time, and disease progress is represented by the area-under-the-disease-progress curve (AUDPC); a higher AUDPC indicates more severe disease progress. The trapezoid rule was used to calculate the AUDPC (Equation 2), following the procedure of Jeger, M. J.; Viljanen-Rollinson, S. L. H. The Use of the Area under the Disease-Progress Curve (AUDPC) to Assess Quantitative Disease Resistance in Crop Cultivars. Theor. Appl. Genet. 2001, 102, 32-40.

$$AUDPC=\Sigma[Y_i+Y_{(i+1)}]/2\times(t_{(i+1)}-t_i) \quad (2)$$

In equation (2), $Y_i$ is the disease severity rating at time, $t_i$.

Figure 9:
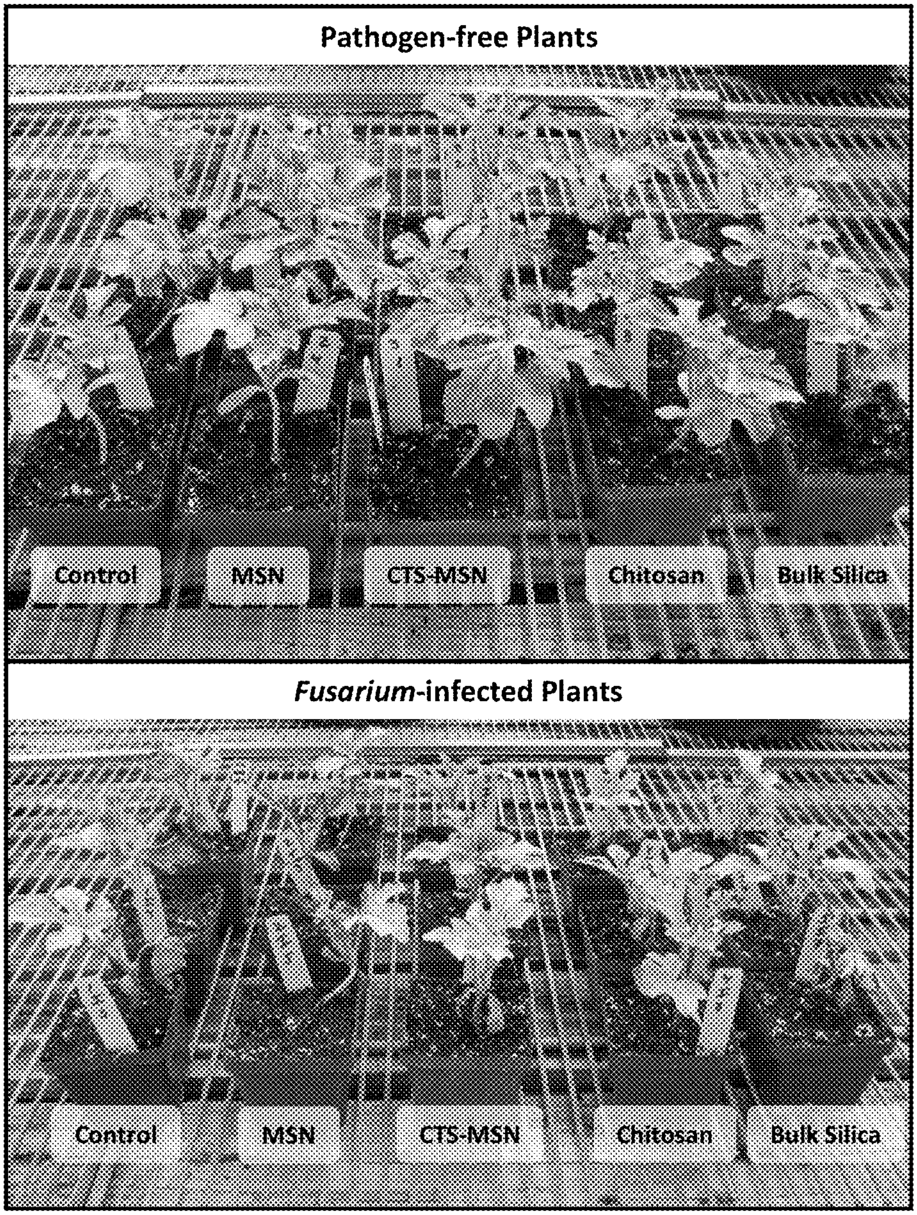
FIG. 9 is photographs of pathogen-free and *Fusarium*-infected plants.

In the greenhouse, plants were rated every 3-4 days beginning approximately 2 weeks days after the beginning of the study. After 5 weeks, the experiment was terminated and the root and shoot biomass were determined. Images of both pathogen-free and *Fusarium*-infected plants after several days can be seen in FIG. 9.

Gene Expression Changes

To monitor changes in the expression of select genes after NP treatment, total plant RNA was extracted from watermelon roots (~0.1 g) with a Sigma-Aldrich Spectrum Plant Total RNA kit (St. Louis, MO); the extracted RNA concentration was measured by a Thermo Scientific Nanodrop Lite Spectrophotometer (Wilmington, DE). A Qiagen QuantiTect Reverse Transcription kit (Velno, The Netherlands) was used for two-step reverse transcription on 1 μg of extracted RNA. RT-qPCR was then used to measure expression of several watermelon genes involved in plant stress and pathogen defense; in addition, several genes relevant in heavy metal regulation are included to facilitate comparison to other studies. A Bio-Rad CFX96 Touch Real-Time PCR Detection System using the fluorescent intercalating dye, SYBR Green (Bio-Rad SsoAdvanced™ Universal SYBR® Green Supermix) was used. The polymerase chain reaction was run by maintaining the samples at 95° C. for 10 min to denature the DNA, and then 40 PCR cycles (95° C. for 15 sec then 60° C. for 60 sec), monitoring the SYBR Green fluorescence at the end of each cycle for DNA quantification. Relative expression of each gene was calculated by $2^{-\Delta\Delta Ct}$ method using Actin as the housekeeping gene.

TABLE 1

List of genes used for gene expression analysis in this work. These genes are orthologs from *Arabidopsis thaliana* that are also found in *Citrullus lanatus*.

| Target Gene | Gene Product | Function | Gene Identifiers |
|---|---|---|---|
| CCH | Copper chaperone | Involved in intracellular copper homeostasis regulation | Cla020497 |
| COX11 | Cytochrome c oxidase assembly protein CtaG/COX11 family | Involved in copper delivery to the COX complex | Cla002392 |
| PAOI | Polyamine oxidase 1 | Polyamine catabolism | Cla015262 |
| RANI | Heavy metal-exporting ATPase | ATP-dependent heavy metal transporter | Cla009875 |
| CSD1 | Copper/zinc superoxide dismutase 1 | Alleviates superoxide radicals | Cla011299 |
| PR1 | Pathogenesis-related protein 1 | Contributes to systemic acquired resistance in plants | Cla001623 |
| PPO | Polyphenol oxidase, chloroplastic-like | Oxidizes phenolic compounds | Cla019486 |
| MDHA | Malate dehydrogenase | Involved in central metabolism and redox homeostasis between organelle compartments | X17362* |
| CYS | Cysteine synthase | Synthesizes L-cysteine, a precursor for glutathione, which is involved in defending against stresses | D28777* |

*These are the NCBI accession numbers for these genes.

Nanoparticle Impact on Biomass

After 65 and 100 days in the field, the fruit of watermelon plants were harvested, and the overall mass from each replicate plant was measured. At the end of the greenhouse experiment, the aboveground tissues and roots were separated, and their mass was measured and compared between treatments. Root systems were divided; half was dried for elemental analysis and half was frozen in liquid nitrogen and then moved to −80° C. until RT-qPCR could be performed. After obtaining the fresh weights of the tissues, they were then dried to constant weight in an oven at 50° C.

Silicon Content in Plant Tissues

To determine whether silicon was accumulating in the treated plants, the aboveground tissues, roots, and fruit were dried to constant weight in a 50° C. oven. The dried tissues were then ground in a mill, and a 0.5 g portion was digested with 5 mL of concentrated nitric acid [Caution: nitric acid is highly corrosive!] for 45 min at 115° C. using a DigiPREP block digestion system (SCP Science, Champlain, NY). The samples were analyzed using an Agilent 7500ce inductively coupled plasma-mass spectrometer (Santa Clara, CA) to determine the silicon content.

RESULTS AND DISCUSSION

Characterization of Chitosan-Coated MSNs

TEM was used to characterize the size of the mesoporous silica nanoparticles and their chitosan-coated counterparts. Three batches of MSNs were coated with chitosan, which had diameters of 36±7, 35±7, and 39±6 nm, as measured from TEM images. Representative TEM images of MSNs before and after coating can be seen in FIG. 1. Since chitosan is organic, its presence is not apparent in these images that rely on mass contrast.

Figure 1B:
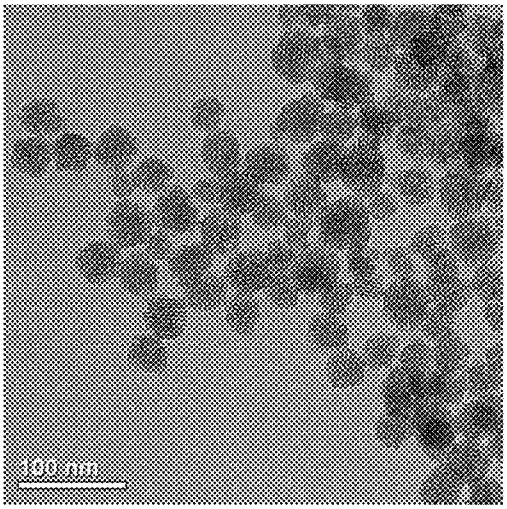
FIG. 1B is a Representative TEM image of MSNs after modification with chitosan (CTS-MSNs).

FIGS. 1A-1B Representative TEM images of a) bare mesoporous silica nanoparticles (MSNs) (FIG. 1A) and MSNs after modification with chitosan (CTS-MSNs) (FIG. 1B).

Figure 2A:
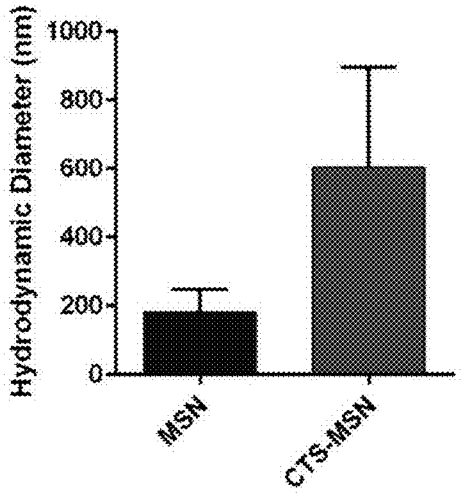
FIG. 2A is a graph of the hydrodynamic diameters before and after application of the chitosan coating.
Figure 2B:
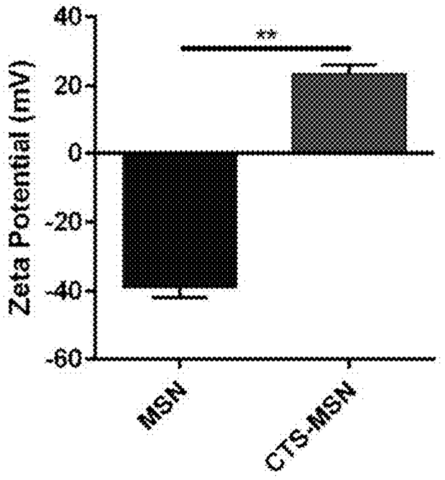
FIG. 2B is a graph of the zeta potential measurement before and after application of the chitosan coating.

The hydrodynamic diameters were measured before and after the chitosan coating, and the ζ-potential measurement was used to confirm the presence of the chitosan coat (FIG. 2A, 2B). Results from the hydrodynamic diameter measurements suggest that the particles may be experiencing slight aggregation after being coated with chitosan. Chitosan is a positively charged polysaccharide; therefore, evidence of its successful coating on MSNs is shown by the zeta potential measurements. Uncoated MSNs have a negative zeta potential (−39±3 mV), while chitosan-coated MSNs have a positive zeta potential (24±2 mV).

Figure 2C:
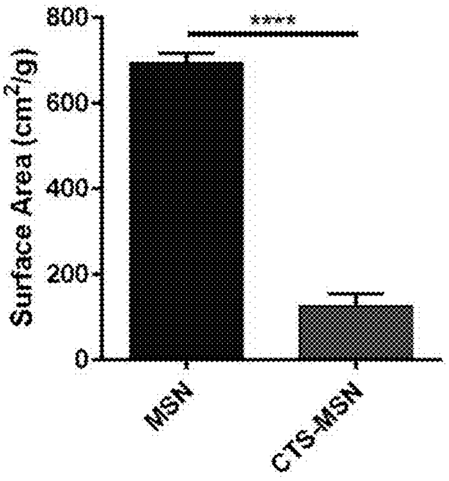
FIG. 2C is a graph of the surface area of the particles before and after application of the chitosan coating.
Figure 2D:
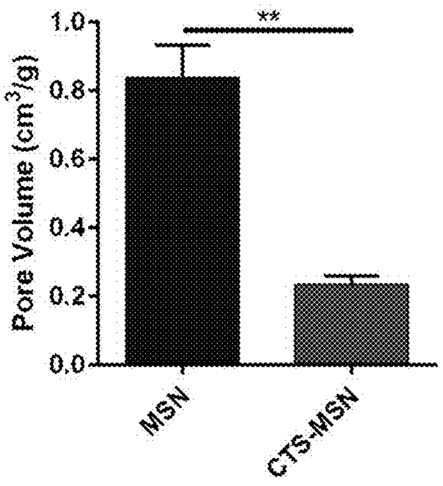
FIG. 2D is a graph of the pore volume before and after application of the chitosan coating.

Nitrogen physisorption was employed to observe the surface area and pore volume change that arose from applying the chitosan coating (FIG. 2C, 2D). A decrease in both surface area and pore volume indicate that the pores of the MSNs are being coated by or filled with the chitosan, decreasing the effective internal surface area of the nanoparticles as well as their overall pore volume. Moreover, the changes that are seen here are similar to those seen in the literature, although differences in the actual values are likely due to differences in the two systems, as the nanoparticles used by Chen and Zhu were also loaded with ibuprofen. (Chen, F.; Zhu, Y. Chitosan Enclosed Mesoporous Silica Nanoparticles as Drug Nano-Carriers: Sensitive Response to the Narrow PH Range. Microporous Mesoporous Mater. 2012, 150 (1), 83-89.) Thermogravimetric analysis was used to determine the mass contribution of chitosan to the chitosan-coated MSNs. While the mass loss profiles collected here look similar to those in the literature, there was increased mass loss from our samples compared to those from Karaman, et al, as there was more chitosan present in our samples. (Karaman, D. S.; Sarwar, S.; Desai, D.; Björk, E. M.; Oddn, M.; Chakrabarti, P.; Rosenholm, J. M.; Chakraborti, S. Shape Engineering Boosts Antibacterial Activity of Chitosan Coated Mesoporous Silica Nanoparticle Doped with Silver: A Mechanistic Investigation. J. Mater. Chem. B 2016, 4, 3292-3304.) Based on evaluation of four replicate samples of CTS-MSNs, approximately 22±7% of the particle mass was from the polysaccharide coating.

Figure 10:
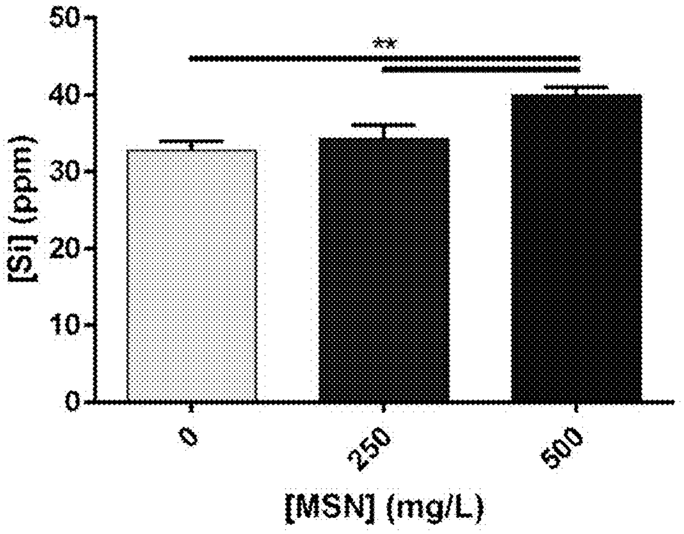
FIG. 10 is a graph of the silicon content of seeds treated with MSN suspensions.

FIG. 2A shows the hydrodynamic diameters as determined before and after application of the chitosan coating. Evidence of successful chitosan coating can be seen in the zeta potential measurement in FIG. 2B, which shows that the bare MSNs had a negative surface charge and after coating, the surface charge was positive. A decrease in the surface area of the particles as shown in FIG. 2C indicates that the pores are covered with chitosan, blocking the interior surface area of the particles, and the pore volume also decreased as shown in FIG. 2D, again due to coverage of the pores by chitosan. The error bars represent the standard deviations from triplicate measurements, and paired t-tests were used to determine statistical significance between the uncoated and coated MSNs. $^{}p<0.01$, $^{}p<0.0001$ Chitosan-coated MSNs Improve Germination of Watermelon Seeds After exposing seeds to the various treatments using a novel vacuum-infiltration technique as described above, the impact on seed germination percentage was assessed, and the AUSGC was calculated. Representative images of seed germination after 11 days can be seen in FIG. 3A**. In seeds that were not infested with *F. oxysporum*, CTS-MSNs improved germination compared to the control at both concentrations tested (FIGS. 3B, 3C). Therefore, we speculate that the improved germination from CTS-MSN treatment may be related to the chitosan content of the particles. This is corroborated by the fact that application of 250 mg/L of chitosan alone also increased germination. A separate study to confirm nanoparticle loading was done with ICP-MS of seeds that had been loaded with MSNs. This showed that seeds that were loaded with the 500 mg/L MSN suspension had significantly more silicon content (a 20% increase) than untreated seeds, and those that had been exposed with 250 mg/L MSN suspension had approximately 7% more silicon (FIG. 10). This demonstrates that nanoparticle loading of the seeds was successful, and it is expected that loading was successful for all of the nanomaterials used in this study. Treatment with chitosan-free MSNs did lead to slightly increased germination, but this increase was not statistically significant, which further corroborates the fact that the additional silicon in the treated seeds is not responsible for the increased germination that was observed. In seeds planted in *Fusarium*-infested soil, germination was not affected by any of the treatments.

Figure 3A:
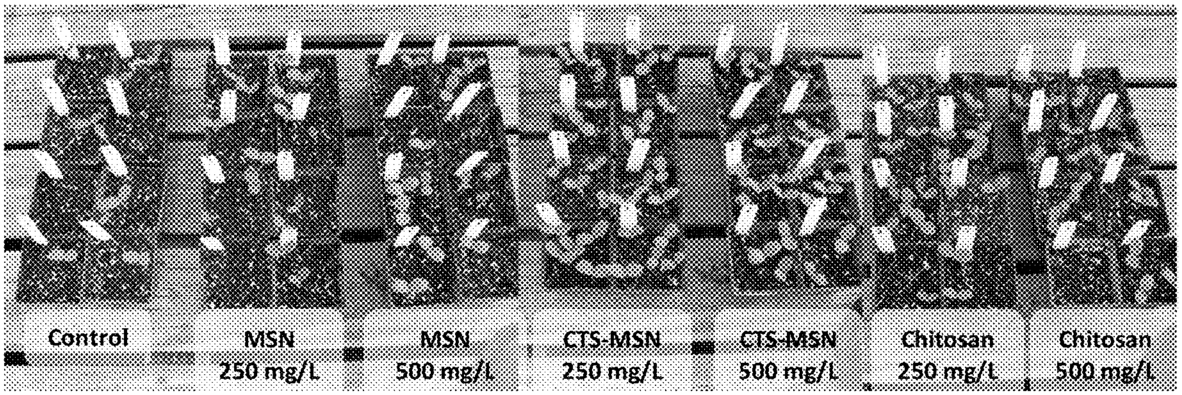
FIG. 3A is a photograph showing the differences in germination after seeds were treated with NP-containing suspensions using a vacuum-infiltration technique.
Figure 3B:
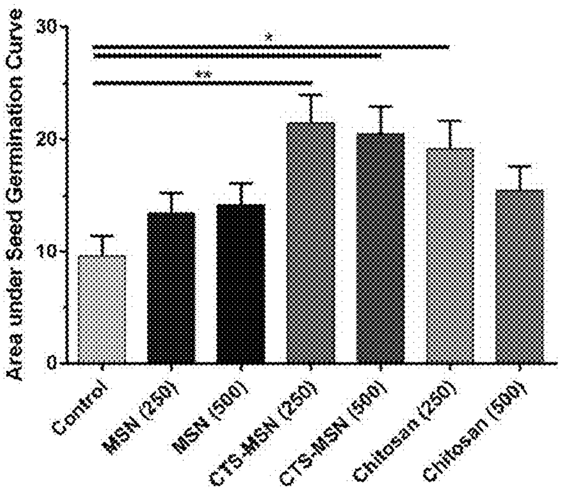
FIG. 3B is a graph of the area-under-the-seed-germination curve of healthy seeds evaluated after various nanoparticle treatments.
Figure 3C:
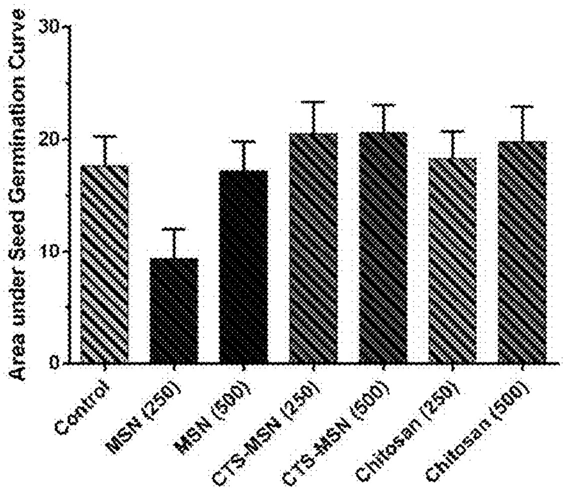
FIG. 3C is a graph of the area-under-the-seed germination curve of seeds planted in *Fusarium*-infested soil.

FIG. 3A consists of images showing the differences in germination after seeds were treated with NP-containing suspensions using a vacuum-infiltration technique. The area-under-the-seed-germination curve was evaluated after treatment. FIG. 3B shows chitosan-coated MSNs improve the germination of seeds in healthy plants, but germination was unaffected in seeds planted in *Fusarium*-infested soil as seen in FIG. 3C. The error bars are the standard error of ten replicates. Statistical testing was performed using a one-way ANOVA with Dunnett's multiple comparisons test. $^{*}p<0.05$, $^{**}p<0.01$ Role in Disease Suppression In the field experiments, the role of MSNs and CTS-MSNs in suppressing *Fusarium* wilt was evaluated by determining the AUDPC (FIG. 4). Not surprisingly, in healthy plants, there was no change in the AUDPC with treatment and no symptoms of infection with *F. oxysporum* were evident. However, with infected plants, treatment of the plants with both MSNs and CTS-MSNs resulted in significant disease suppression (disease progress was reduced by ~40% and 27% for MSN and CTS-MSN treatment, respectively) over the experiment. Since both types of particles are exerting benefit, it is clear that the delivery of silica to the plant is critical to the observed disease suppression. For the CTS-MSNs, it is also possible that the presence of chitosan is helping to stimulate the defense response of the plants against *Fusarium* wilt. However, the lack of response in the MSN-free chitosan control suggests that association with the MSN is driving the observed activity. It should be noted that bulk silica treatment does not suppress *Fusarium* wilt, indicating the importance of the nanoscale size regime for the silica treatment to have an impact.

Figure 4A:
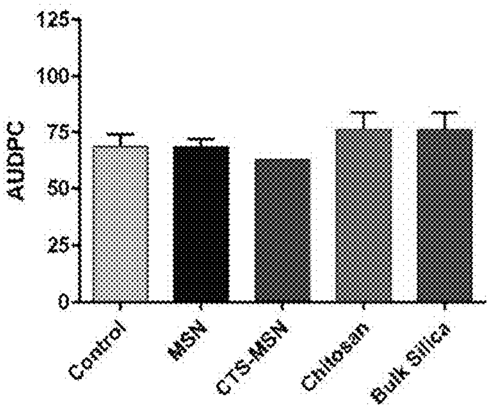
FIG. 4A is a graph of the area-under-the-disease-progress curve (AUDPC) of healthy plants following various nanoparticle treatments.
Figure 4B:
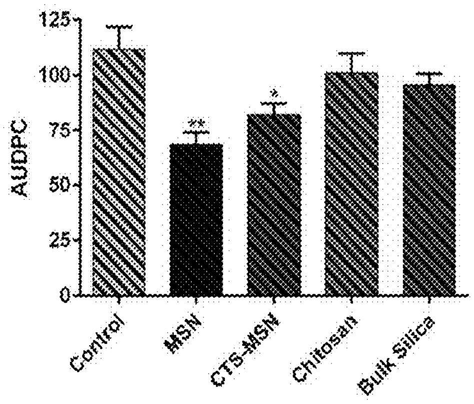
FIG. 4B is a graph of the AUDPC of *Fusarium*-infected plants following various nanoparticle treatments.
Figure 5:
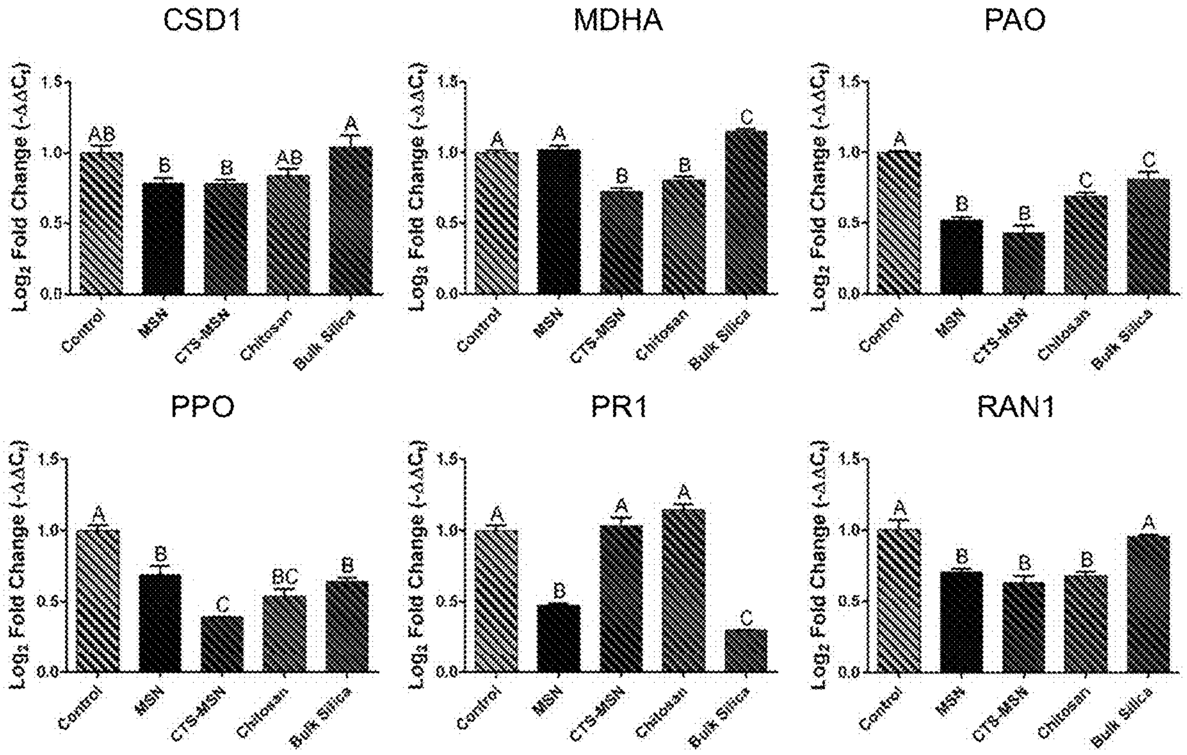
FIG. 5 is graphs of gene expression levels for CSD1, MDHA, PAO, PPO, PR1, and RAN1 after various nanoparticle treatments.

FIG. 4A shows that in healthy plants, there is no difference in AUDPC following nanoparticle treatment. FIG. 4B shows that for *Fusarium*-infected watermelon, both MSNs and CTS-MSNs enhance disease suppression of *Fusarium* wilt. The error bars represent the standard error from six plants, with statistical significance testing done using a one-way ANOVA with Dunnett's multiple comparisons test to compare effects of the different treatments to the control. $^{*}p<0.05$, $^{}p<0.01$ Gene Expression Changes The expression of several genes related to plant defense was investigated to gain a more fundamental understanding of the impact of the treatments (FIG. 5**). Notably, for many genes that are related to stress (CSD1, PAO, PPO, RAN1), treatment with MSNs, CTS-MSNs, or chitosan showed decreased expression. For PAO and PPO, reduced expression is also evident after treatment with bulk silica. The decreased expression in these genes suggests that the various treatments yielded some alleviation of the biotic stress of disease in these *Fusarium*-infected plants. This corroborates the reduced disease progress observed in the field after exposure of the plants to the nanoparticles. The expression of another stress-related gene, MDHA, was also reduced in plants that were treated with CTS-MSNs and chitosan. The similarity in expression after CTS-MSN and chitosan treatment suggests that the chitosan portion of CTS-MSNs is contributing to the stress-reducing mechanism. Interestingly, increased expression of MDHA is seen in bulk silica-treated plants, indicating greater stress from *Fusarium* wilt infection. There were no changes in CCH or COX 11 expression (FIG. 5); both of these are genes pertaining to maintenance of copper homeostasis and delivery of copper to cytochrome c oxidase complexes in the plant, respectively. There was also no change in expression of CYS (FIG. 5), which is related to stress reduction in plants, but indirectly, as this gene encodes a compound that serves as a precursor for a different stress-related pathway. It is important to note that the expression of these genes was assessed at the end of the experiment. Since gene expression profiles of the plants can change based on age and life-cycle stage of the plant and on the time course of infection, it is possible that the stress-related genes may have been differentially modulated earlier in the infection process for treated plants. However, by the end of the experiment when these measurements were taken, the reduced disease burden on treated plants could lead to reduced expression of stress-related genes.

FIG. 5 shows gene expression levels for CSD1, MDHA, PAO, PPO, PR1, and RAN1. The error bars represent the standard error from three replicates. Statistical significance was determined for each gene using a one-way ANOVA with Tukey's multiple comparisons test. Each sample with a different letter above indicates statistically significant differences with at least $p<0.05$.

Impact of Chitosan-Coated MSNs on Fruit Yield

Figure 6A:
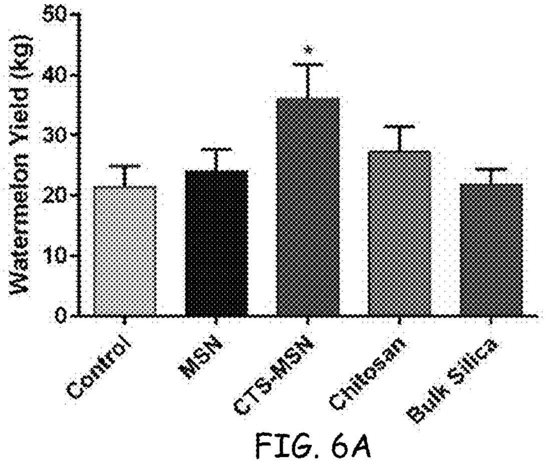
FIG. 6A is a graph of the fruit yield of pathogen-free watermelon plants after various nanoparticle treatments.
Figure 6B:
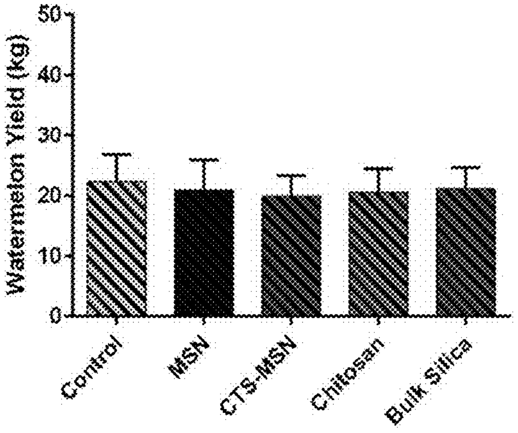
FIG. 6B is a graph of the fruit yield of *Fusarium*-infected watermelon plants after with various nanoparticle treatments.
Figure 7A:
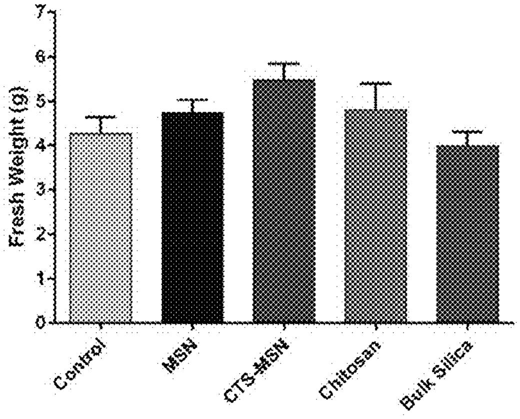
FIG. 7A is a graph of the fresh weight of the aboveground tissues of healthy plants after various nanoparticle treatments.
Figure 7B:
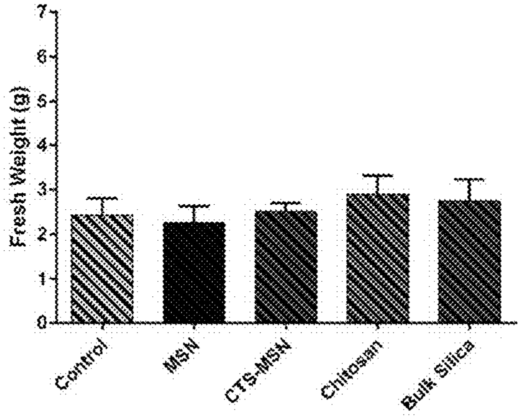
FIG. 7B is a graph of the fresh weight of the aboveground tissues of *Fusarium*-infected plants after various nanoparticle treatments.
Figure 7C:
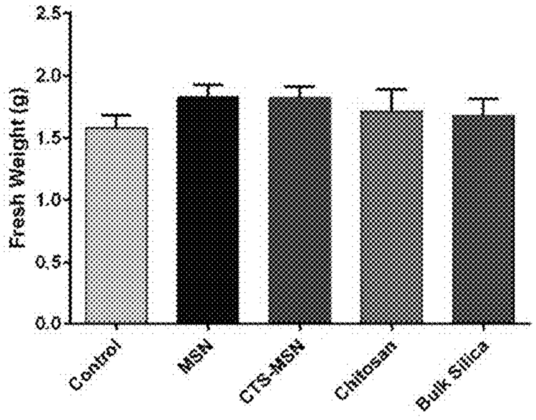
FIG. 7C is a graph of the fresh weight of the roots of healthy watermelon plants after various nanoparticle treatments.
Figure 7D:
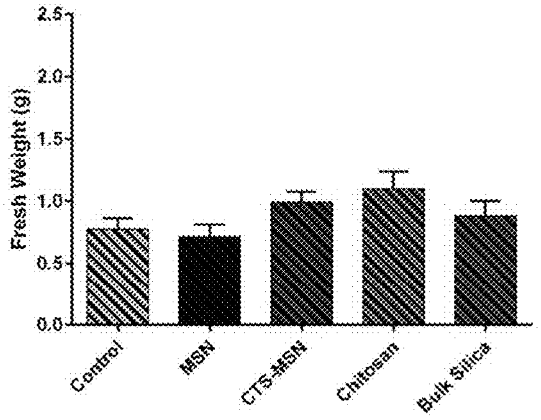
FIG. 7D is a graph of the fresh weight of the roots of *Fusarium*-infected plants after various nanoparticle treatments.
Figure 8A:
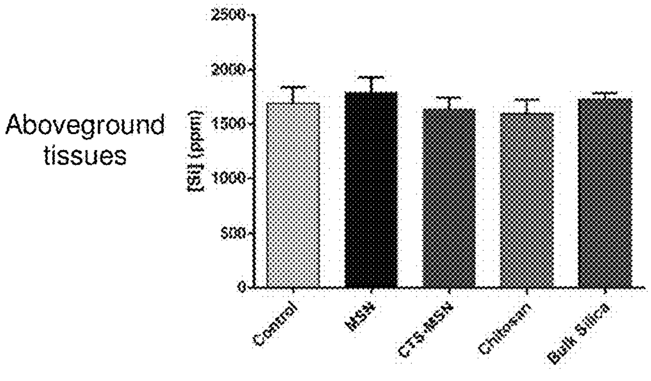
FIG. 8A is a graph of the silicon content of aboveground tissues of healthy plants after various nanoparticle treatments.
Figure 8B:
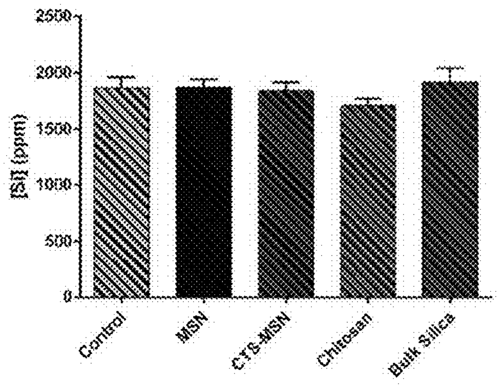
FIG. 8B is a graph of the silicon content of aboveground tissues of *Fusarium*-infected plants after various nanoparticle treatments.
Figure 8C:
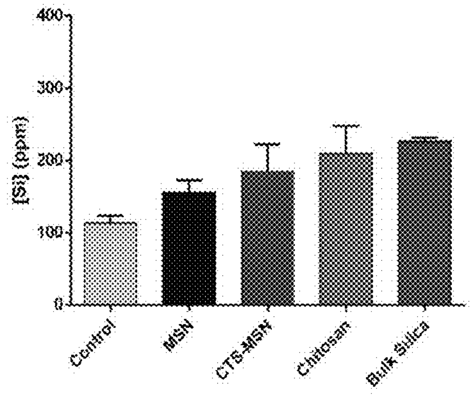
FIG. 8C is a graph of the silicon content in the roots of healthy plants after various nanoparticle treatments.
Figure 8D:
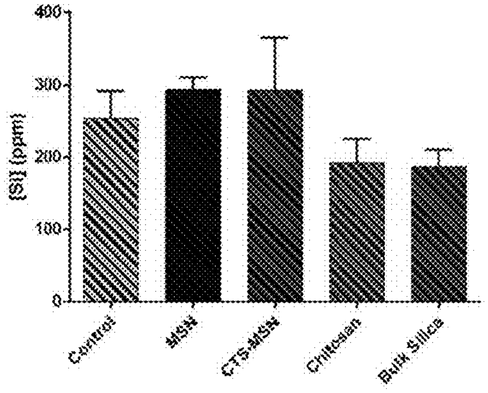
FIG. 8D is a graph of the silicon content in the roots of *Fusarium*-infected plants after various nanoparticle treatments.
Figure 8E:
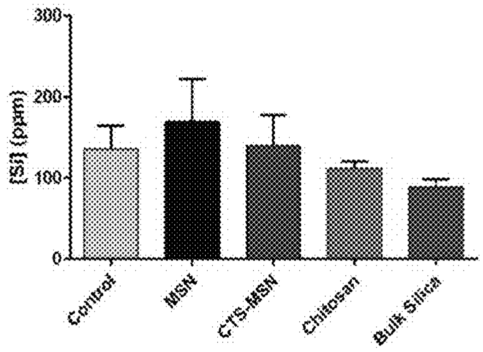
FIG. 8E is a graph of the silicon content in the edible portion of the fruits of healthy plants after various nanoparticle treatments.
Figure 8F:
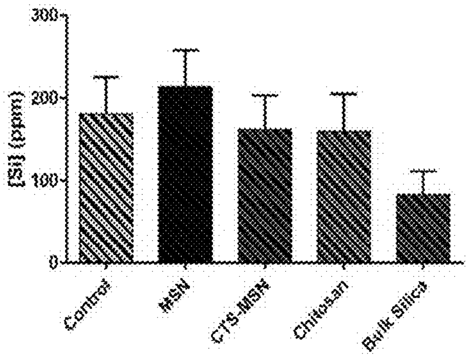
FIG. 8F is a graph of the silicon content in the edible portion of the fruits of *Fusarium*-infected plants after various nanoparticle treatments.

Since disease reduction was observed for plants treated with MSNs and CTS-MSNs, it was hypothesized that these particles would improve the overall fruit yield. Fruits were harvested from plants 65 and 100 days post-planting, and the cumulative watermelon yield is shown (FIG. 6A, 6B). A single application of 1-2 mL of 500 mg/L CTS-MSNs to each healthy plant, via seedling dipping into the nanoparticle suspension, led to a 70% increase in watermelon yield, whereas none of the treatments applied to plants infected with *Fusarium* wilt caused any appreciable change in fruit production. Since the number of fruits produced was relatively unchanged between treatments, this indicates that CTS-MSNs have significant potential for stimulating the yield of fruit under disease-free conditions. It is worth emphasizing that this increase in fruit yield was measured months after an initial treatment of the seedlings using a low amount of material (0.5-1 mg applied per plant). The lack of effect on plants grown with the pathogen in both locations is somewhat surprising given that the MSN treatments were effective in reducing disease severity in the greenhouse. We recognize that the supply of silicon to the plant occurred only at the seedling stage and that the yield enhancing effects were reduced. Multiple nanoparticle applications during growth may circumvent this obstacle. It is also possible that field variability and interaction of the pathogen with other stressors such as insects or minor pathogens could have overwhelmed any ameliorating effect of MSN treatment. Another factor may have been the excessive rainfall experienced in 2018, where the total rainfall for where the watermelon were grown during June, July, August, and September was twice the normal average and could have exacerbated the disease to the point where early life stage benefits of the MSNs were ineffective. Additional MSN applications during growth may be valuable as they would ensure a more continuous silicic acid supply and stimulate additional disease suppression.

As shown in FIG. 6, when applied to a) pathogen-free watermelon plants that were grown at either of two locations (Griswold, CT or Hamden, CT), CTS-MSNs are showing a significant increase in the watermelon yield that is not seen from any of the other treatments. For b) *Fusarium*-infected watermelon plants, no change in yield of fruit is seen for any of the nanoparticle treatments used. The error bars are from the standard error of twelve replicates. Statistical testing was performed with a one-way ANOVA with Dunnett's multiple comparisons test to compare the treatment effects to the control plants. $^{*}p<0.05$ Changes in Biomass after NP Exposure Plant biomass was monitored in the greenhouse as another means of assessing the overall plant health in diseased and healthy conditions as a function of the treatments. Although the biomass measurements were statistically equivalent (FIG. 7A-7D), the trends reflect the field findings where MSN and CTS-MSNs improve growth in the absence of the pathogen. The lack of significant differences is due to plant-to-plant variability. Similar trends were observed with the dry weights (data not shown). This result is somewhat surprising given the reduced disease progression by MSNs and CTS-MSNs seen above; however, given that the treatments were done when the plants were seedlings, differences in biomass may be masked after the several weeks of growth that had occurred by the time these measurements were taken. The variability that has been observed is likely due to the use of a single application of nanoparticles, so that differences in response during subsequent growth and infections that can be observed weeks later are not surprising. This may suggest that use of multiple treatments over the growing period would be beneficial to maximize the benefits of the nanoparticles.

The fresh weight of the aboveground tissues of healthy plants (FIG. 7A) and *Fusarium*-infested plants (FIG. 7B); the roots of healthy watermelon plants (FIG. 7C) and infected plants (FIG. 7D) is unchanged regardless of the applied treatment. The error bars represent the standard error of ten replicate plants. A one-way ANOVA with Tukey's multiple comparisons test was used to evaluate statistical significance.

Silicon Content

At harvest, the silicon content of aboveground tissues, roots, and fruits were measured using ICP-MS (FIGS. 8A-8F). In all of the tissues tested, the silicon content in the treatment groups was not statistically distinct from that of the control plants. This is likely due to the silicon being diluted during subsequent growth that followed after the young seedling was exposed to MSNs. That being said, there is a non-significant trend in the root data (FIG. 8C) suggesting a slight increase in silicon incorporation in the roots of healthy *C. lanatus* after treatments. The lack of increased silicon presence in the edible portions of the fruits is notable, as this indicates that the applied nanoparticles or the released silicic acid are not likely entering the edible tissues at any appreciable rate when compared to untreated controls. This may suggest there is minimal risk associated with the consumption of fruit from plants treated with silica nanoparticles.

The silicon content in the aboveground tissues of a) healthy plants (FIG. 8A) and infected plants (FIG. 8B) is unchanged by the nanoparticle application. The silicon content in the roots of healthy (FIG. 8C) and *Fusarium*-infested (FIG. 8D) *C. lanatus* is also unchanged. The edible portion of the fruits of watermelon plants has no appreciable change in silicon content for healthy (FIG. 8E) and infected (FIG. 8F) plants. The error bars represent the standard error of five replicates. Statistical testing was performed using a one-way ANOVA with Tukey's multiple comparisons post hoc test.

Conclusions

This is the first example where high surface area silica and chitosan were combined to enhance the health of crop plants. The approximately 70% increase in fruit yield from healthy plants after a single application of CTS-MSNs to seedlings prior to transplant demonstrates the utility of these materials to contribute to increased food production from plants, suggesting that there may be economic incentive to supplying watermelon plants with these particles. Furthermore, the increased germination of seeds that had been vacuum-infiltrated with CTS-MSNs is yet another indication that these nanoparticles have benefits to healthy plants. To plants that were infected with *Fusarium* wilt, a single application of MSNs or CTS-MSNs reduced disease progress, which was corroborated by gene expression data that showed reduced expression of stress genes in *C. lanatus*. Gene expression data also suggested that the presence of chitosan is contributing to the benefits of CTS-MSNs, as expression of stress-related genes was similar between plants that had been treated with CTS-MSNs and with chitosan alone. ICP-MS analysis of plant tissues did not reveal an accumulation of silica in the plants (due to growth dilution after initial exposure), and importantly, there was also no accumulation of silica in the edible tissues of the fruit, demonstrating that there should be minimal risk in their consumption. It is impressive that these benefits are observed in fully grown plants after a sub-milligram-dose was applied when the plants were young seedlings. To promote disease suppression and plant growth even further in future work, the treatments will be applied to the seeds as well as the seedlings multiple times over the course of the growing period. Given that the plant treatments require only a small amount of material (0.5-1 mg per plant), multiple treatments still present a rather sustainable option for agricultural use. The sustainability is further enhanced by the high earth abundance of the precursor materials used.

The invention claimed is:

1. A method for improving yield in a member of the family Cucurbitaceae, the method comprising:

Applying mesoporous silica nanoparticles combined with chitosan without nutrients or micronutrients directly to a seed or directly to a plant of the member of the family Cucurbitaceae.

2. The method of claim 1 wherein the member of the family Cucurbitaceae comprises *Citrullus lanatus*.

3. The method of claim 2 wherein the plant of the *Citrullus lanatus* demonstrated reduced expression of stress-related genes.

4. The method of claim 1 wherein the member of the family Cucurbitaceae comprises *Citrullus lanatus* and wherein the *Citrullus lanatus* exhibited an increased fruit production of approximately at least 70%.

5. The method of claim 1 wherein the mesoporous silica nanoparticles were applied to the plant of the member of the family Cucurbitaceae by foliar exposure to a mesoporous silica nanoparticle suspension to coat leaves of the plant with the mesoporous silica nanoparticle suspension.

6. The method of claim 1 wherein the mesoporous silica nanoparticles were applied to a seed of the member of the family Cucurbitaceae by infusing the seed with a mesoporous silica nanoparticle suspension.

7. A method for combating *Fusarium* wilt in a member of the family Cucurbitaceae, the method comprising:

Applying mesoporous silica nanoparticles coated with chitosan without nutrients or micronutrients directly to a seed or directly to a plant of the member of the family Cucurbitaceae.

8. The method of claim 7 where the member of the family Cucurbitaceae comprises *Citrullus lanatus*.

9. The method of claim 8 wherein the plant of the *Citrullus lanatus* demonstrated reduced expression of stress-related genes.

10. The method of claim 8 wherein the plant of the *Citrullus lanatus* exhibited an increase of approximately at least 70% in fruit by weight.

11. The method of claim 7 wherein the mesoporous silica nanoparticles were applied to the plant of the member of the family Cucurbitaceae by foliar exposure in a mesoporous silica nanoparticle coated with chitosan suspension to coat leaves of the plant with the mesoporous silica nanoparticle coated with chitosan suspension.

12. The method of claim 7 wherein the mesoporous silica nanoparticles coated with chitosan were applied to the seed of the member of the family Cucurbitaceae by infusing the seed with the mesoporous silica nanoparticle coated with chitosan suspension.

13. A method of infusing seeds from a member of the family Cucurbitaceae with mesoporous silica nanoparticles, the method comprising:

Providing a suspension of mesoporous silica nanoparticles coated with chitosan without nutrients or micronutrients;

Placing the seeds in the mesoporous silica nanoparticle coated with chitosan suspension;

Positioning the seeds in the mesoporous silica nanoparticle coated with chitosan suspension in a vacuum chamber where a vacuum is pulled; and Releasing the vacuum thereby infusing the seeds with the mesoporous silica nanoparticle coated with chitosan suspension.

14. The method of claim 13 and further comprising planting the seeds in a growing medium wherein increased germination of the seeds results when compared to seeds that have not been infused with the mesoporous silica nanoparticle coated with chitosan suspension.

15. The method of claim 13 wherein the member of the family Cucurbitaceae comprises *Citrullus lanatus*.

16. An agricultural amendment comprising mesoporous silica nanoparticles in combination with chitosan without nutrients or micronutrients for application directly to a seed or directly to a plant.

* * * * *